United States Patent
Komvopoulos et al.

(10) Patent No.: US 6,685,743 B2
(45) Date of Patent: Feb. 3, 2004

(54) PLASMA-ASSISTED SURFACE MODIFICATION OF POLYMERS FOR MEDICAL DEVICE APPLICATIONS

(75) Inventors: Kyriakos Komvopoulos, Orinda, CA (US); Catherine M. Klapperich, San Francisco, CA (US); Lisa A. Pruitt, Oakland, CA (US); Stephen L. Kaplan, San Carlos, CA (US)

(73) Assignee: The Regents of the University of California, Oakland, CA (US)

( * ) Notice: Subject to any disclaimer, the term of this patent is extended or adjusted under 35 U.S.C. 154(b) by 25 days.

(21) Appl. No.: 10/075,813

(22) Filed: Feb. 12, 2002

(65) Prior Publication Data

US 2003/0040807 A1 Feb. 27, 2003

Related U.S. Application Data

(62) Division of application No. 09/450,815, filed on Nov. 29, 1999, now Pat. No. 6,379,741.
(60) Provisional application No. 60/110,188, filed on Nov. 30, 1998.

(51) Int. Cl.[7] ................................. A61F 2/30
(52) U.S. Cl. .................................... 623/18.11
(58) Field of Search ...................... 623/18.11

(56) References Cited

U.S. PATENT DOCUMENTS

| 3,992,725 A | * 11/1976 | Homsy ................. 424/423 |
| 4,656,083 A | 4/1987 | Hoffman et al. |
| 4,919,659 A | 4/1990 | Horbett et al. |
| 5,080,924 A | 1/1992 | Kamel et al. |
| 5,091,204 A | 2/1992 | Ratner et al. |
| 5,344,449 A | 9/1994 | Christ et al. |
| 5,981,827 A | 11/1999 | Devlin et al. |
| 6,017,975 A | 1/2000 | Saum et al. |
| 6,131,580 A | * 10/2000 | Ratner et al. ........... 128/898 |

FOREIGN PATENT DOCUMENTS

| WO | WO 95/21212 | 8/1995 |
| WO | WO 99/52474 | 10/1999 |

OTHER PUBLICATIONS

Klapperich et al., *Mat. Res. Symp. Soc. Proc.* (1999) 550: 331–336.
Kurtz et al., *Biomaterials* (1999) 20: 1659–1688.
*The Adult Hip* (1998) Eds. J.J. Callaghan et al., Chap. 7, S. Li, "Polyethylene," 2: 105–122.
Li and Burnstein, *The Journal of Bone and Joint Surgery* (1994) 76–A(7): 1080–1090.

* cited by examiner

Primary Examiner—Pedro Philogene
Assistant Examiner—D. Austin Bonderer
(74) Attorney, Agent, or Firm—M. Henry Heines; Townsend and Townsend and Crew LLP

(57) ABSTRACT

The surface of a high molecular weight polymer such as high molecular weight polyethylene is modified in a localized manner by treatment with a plasma gas. The treatment produces a variety of useful results, depending on the gas used and the treatment conditions. One such result is crosslinking of the polymer in a localized manner at the surface to improve the durability of the surface against detrimental processes such as reorientation and alignment of the crystalline lamellae parallel to the contact surface which renders the surface susceptible to disintegration into particles. Another result is the chemical transformation of the surface for purposes such as increasing the hydrophilic or hydrophobic nature of the surface or coupling functional groups to the surface.

14 Claims, 6 Drawing Sheets

PLASMA-ASSISTED SURFACE MODIFICATION OF POLYMERS FOR MEDICAL DEVICE APPLICATIONS

CROSS-REFERENCE TO RELATED APPLICATION

This application is a division of U.S. patent application Ser. No. 09/450,815 filed Nov. 29, 1999 now U.S. Pat. No. 6,379,741, now allowed, which is related to U.S. Provisional Patent Application No. 60/110,188, filed Nov. 30, 1998, and claims all benefits legally available therefrom. Patent application Ser. No. 09/450,815 and Provisional Patent Application No. 60/110,188 are hereby incorporated by reference for all purposes capable of being served thereby.

STATEMENT OF GOVERNMENT RIGHTS TO INVENTION DUE TO FEDERAL SPONSORSHIP

The invention was made with Government support under Grant (Contract) No. N00014-98-1-0633 awarded by the Office of Naval Research, and Grant (Contract) No. CMS-9624978 awarded by the National Science Foundation. The Government has certain rights to this invention.

BACKGROUND OF THE INVENTION

1. Field of the Invention

This invention lies in the field of medical devices such as artificial knee and hip joints. In particular, this invention addresses matters associated with the use of ultra high molecular weight polyethylene (UHMWPE) and other biologically compatible polymers suitable for use in the manufacture of such devices.

2. Background of the Invention

Polymers are widely used as materials of construction in medical devices such as artificial joints, bio-instruments, and other medical implants. Knee joint replacements, many of which use UHMWPE as the tibia component, are examples of such devices. Unfortunately, artificial knees and other articulated implants have a limited life span in the body since the wear on the UHMWPE component causes the material to deteriorate and to form debris which leads to inflammation and osteolysis. Other factors that limit the life span of UHMWPE and other polymers used in these devices are cyclic damage, contact stresses, friction, and possibly the hydrophilic/hydrophobic character which may affect biocompatibility. Whatever the cause, the device ultimately reaches the end of its life span and a replacement is needed. Unfortunately, replacement surgery (which is termed a "revision" operation) is often more difficult and poses a higher risk than the original implantation surgery. Nearly 500,000 artificial joints are implanted in the United States each year, and the average artificial joint lasts about 15 years before it must be replaced. This time span suggests that a single implantation may be suitable for older or less active patients. Young, active patients however may require one or more revisions, and the number of revisions increases with the increase in the life expectancy of the general population. Aware of the low success rate of revisions, many younger patients wait (often in pain) before their first arthroplasty operation in order to lessen the number of revisions that they will need during their lifetime.

The development of sophisticated techniques such as transmission electron microscopy for characterizing surfaces has led to an improved understanding of wear mechanisms. As the polymer is subjected to wear, the polymer delaminates and particles of the polymer separate from the component. The separated particles are then released into the surrounding tissue. Crystalline lamellae that are part of the polymer structure are particularly susceptible to the shear forces that arise when the contacting surfaces slide against each other, since these shear forces cause the lamellae to align at the surface, which increases their susceptibility to breakage. This causes further particle formation and separation.

Several theories have been advanced to explain the mechanisms by which wear occurs in the UHMWPE used in total joint prostheses. Some of these theories are described by Dumbleton, J. H., et al., in "The Wear Behavior of Ultrahigh Molecular Weight Polyethylene," *Wear*, vol. 37, pp. 279–289 (1976); Nusbaum, H. J., et al., in "Wear Mechanisms for Ultrahigh Molecular Weight Polyethylene in the Total Hip Prosthesis," *J. Appl. Polymer Sci.*, vol. 23, pp. 777–789 (1979); and Engh, G. A., et al., in "Polyethylene Wear Metal-Backed Tibial Components in Total and Unicompartmental Knee Prostheses," *Journal of Bone and Joint Surgery*, vol. 74-B, pp. 9–17 (1992). According to these theories, prostheses containing a UHMWPE component in articulating contact a metal or metal alloy component undergo both adhesive and abrasive wear. Material is disengaged from the surface of the UHMWPE component by asperities of the metal component or by third-body abrasion when previously separated particles are drawn across the contact interface. Additional theories cite the occurrence of surface and subsurface cracking caused by high contact stresses at the surface. Subsurface cracks propagate through the material and join other subsurface and surface cracks, leading to delamination and the deterioration of the delaminated material into particulate debris.

The particles released during the wear of UHMWPE components in total knee replacements are on the order of 1 micron in size. Particles of this size elicit an immune response in neighboring tissues. Since giant cells (macrophages) generally do not metabolize such particles, the particles remain in the physiological system and lead to chronic inflammation and pain. Fatigue due to subsurface cracks may itself lead to catastrophic failure, but fatigue coupled with wear is generally the greatest life-limiting factor. Debris from frictional sliding between the polymeric and metallic surfaces of the implant leads to clinical complications long before the materials fail due to macroscopic fatigue.

Immune reactions from particulate debris and mechanisms by which these reactions lead to osteolysis or accelerated bone re-absorption are reported by Schmalzried, T. P., et al., "Polyethylene Wear Debris and Tissue Reactions in Knee as Compared to Hip Replacement Prostheses," *Journal of Applied Biomaterials*, vol. 5, pp. 180–190 (1994); and Lewis, G., "Polyethylene Wear in Total Hip and Knee Replacement," *Journal of Biomedical Materials Research*, vol. 38, pp. 55–75 (1997). Osteolysis leads to degradation of the anchoring bone, making revision surgery more difficult if not impossible, as reported by Howie, D. W., "Tissue Response in Relation to Type of Wear Particles Around Failed Hip Arthroplastics," *J. Arthroplasty*, vol. 5 (1990). The effect of particles entering the lymph nodes is largely unknown.

Other investigators have examined the material properties of the femoral component and have suggested a range of possible alternative materials and surface modifications, as discussed in Ratner, B. D., et al., *Polymer Surfaces and Interfaces*, edited by Feats, W. J., et al., John Wiley, Chichester, UK, pp. 231–251 (1987); Davidson, J. A., et al., "Surface Modification Issues for Orthopedic Implant Bearing Surfaces," *Materials and Manufacturing Processes,* vol. 7, pp. 405–421 (1992); and Walker, P. S., et al., "Wear Testing of Materials and Surfaces for Total Knee Replacement," *Journal of Biomedical Materials Research,* vol. 33, pp. 159–175 (1996).

Further disclosures of potential relevance to this invention are descriptions of the use of radio frequency power sources used to energize a gas to produce a plasma as disclosed in Kolluri, O. S., "Plasma Surface Engineering of Plastics for Medical Device Applications," *Materials Plastics and Biomaterials* (1995). The effect of high concentrations of $CF_3$ groups on the surface of UHMWPE in promoting the binding of proteins is described by Castner, D. G., et al., "RF Glow Discharge Deposition of Fluorocarbon Films for Enhanced Protein Adsorption," *Annual Meeting Society for Biomaterials,* San Francisco, Calif., p. 218 (Mar. 18–22, 1995).

SUMMARY OF THE INVENTION

It has now been discovered that prosthetic implants with components made of UHMWPE or other high molecular weight polymers that suffer the disadvantages enumerated above can be improved by treating the surface of the polymeric component with a plasma gas to produce various conversions or modifications of the polymer at and near the surface. By appropriate selection of the plasma gas and the conditions of treatment, one can select a particular conversion or modification to address a particular problem or to benefit the polymeric component and the implant as a whole in any of a variety of ways, such as improving wear resistance, reducing the tendency toward the release of particular debris, lessening friction between the polymeric component and an adjacent component, increasing either the hydrophilic character or the hydrophobic character of the polymer surface, modifying the chemistry of the surface by attaching functional groups, sterilizing the surface, roughening the surface, or making it more biocompatible.

One conversion achievable by the practice of this invention is crosslinking of the polymer at the surface. This improves the wear resistance of the polymer by reducing or eliminating the tendency of the polymer chains and the crystalline lamellae to align at the surface and thus reducing their susceptibility to breakage into particles. Conversely, it has been discovered that crosslinking throughout the bulk of the polymer is not beneficial, since it lowers the resistance of the polymer to crack propagation and thereby renders the polymer component more susceptible to fatigue. Crosslinking in a concentrated manner at the surface, and preferably also in regions near the surface with a crosslinking density that decreases with increasing distance from the surface, thus improves the wear resistance without substantial loss of component fatigue resistance.

Other conversions achievable by the practice of this invention, either in conjunction with or independent of crosslinking, are coupling reactions between the polymer surface and the plasma gas. Included among these reactions are the covalent attachment of groups to the surface, using groups that have particular functionalities or hydrophobic or hydrophilic characteristics that benefit the longevity or utility of the polymer as a component of the implant, or the compatibility of the polymer with the surrounding tissue. The plasma reagent may thus be one that places hydroxyl groups or other hydrophilic groups on the polymer surface, or one that places hydrophobic organic groups or low-friction fluorocarbon groups on the surface. The lowering of friction achieved by the covalent attachment of fluorocarbon groups when combined with surface crosslinking is particularly effective in minimizing shear deformation, bulk fractures, and surface delamination of the polymeric component. This in turn reduces and possibly eliminates the presence of loose particles, the loosening of joints, and the re-adsorption of bone.

Plasma treatment in accordance with this invention can thus be used to modify the surface chemistry and microstructure of the polymeric component of an implant in ways that will benefit the component and the implant, and treatments producing two or more effects can be performed simultaneously or in sequence. The treatments can also be combined with additional treatments for supplementary purposes such as a preliminary sterilization of the component. These and other features, advantages, and aspects of the invention are described below in detail.

DETAILED DESCRIPTION OF THE INVENTION AND PREFERRED EMBODIMENTS

Figure 1:
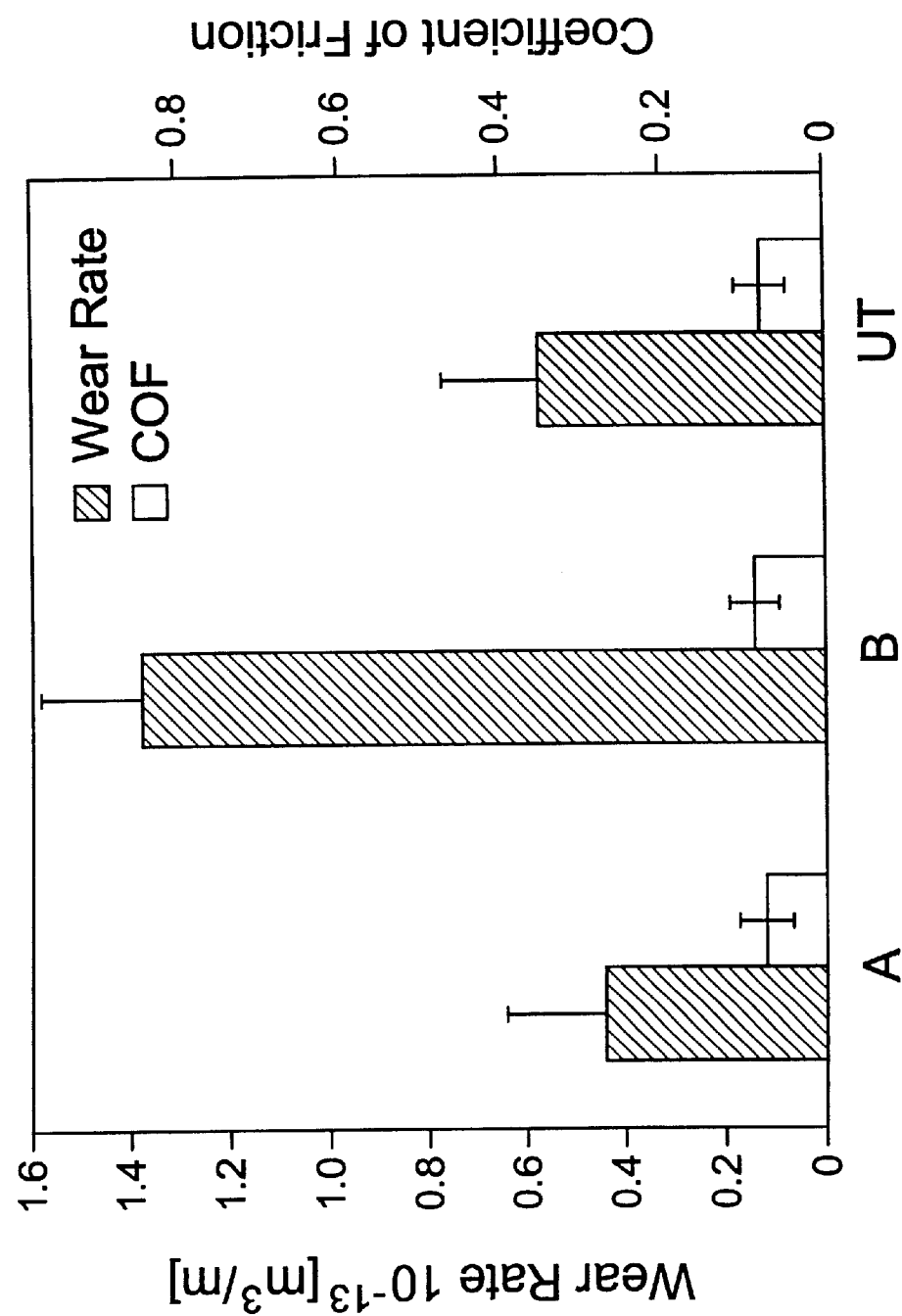
FIG. 1 is a bar graph showing experimental results in terms of wear rate and coefficient of friction, showing the effect of this invention by comparing test samples of UHMWPE treated in accordance with this invention with untreated samples.

Plasma treatments of a polymeric workpiece in accordance with this invention are achieved by placing the workpiece in contact with the gas to be used in the treatment and imposing high-energy radiation, preferably radio-frequency radiation, sufficient to ionize the gas to a plasma state. While not intending to be bound by any particular theory or mechanism of operation, it is believed that the plasma activates the polymer chains that are in contact with the plasma by dissociating covalent bonds in the polymer chains to form free radicals that are reactive with each other or with free radicals in the plasma gas itself. The reactions that then occur at these activated sites will vary with the type of gaseous substance used to form the plasma, or with operating conditions such as the power density, exposure time, working pressure, gas flow rate, temperature, electrode spacing, chamber dimensions, substrate bias voltage, or combinations of these conditions. The activation of the polymer by dissociation of its covalent bonds prior to crosslinking or to a coupling reaction with the plasma gas may be performed as a preliminary activation step or simultaneously with the crosslinking or coupling reaction. Likewise, crosslinking may be performed as a preliminary step to coupling, or crosslinking and coupling may be performed simultaneously. When the procedure is performed as two or more steps in sequence, different treatment gases may be used for each step, or the same gas may be used but with different operating conditions such as, for example, a stepwise change in power density. The choice of treatment, whether crosslinking, an increase in the hydrophilic or hydrophobic character, or the coupling of functional groups of various kinds, will depend on the use contemplated for the treated polymer, whether as part of a prosthetic implant, a diagnostic or therapeutic medical device, or as a substrate for proteins or biological cells in a laboratory or clinical procedure. Appropriate treatments can be selected for any of various transformations of the surface, including enhancing the shear strength of the component, lowering the friction coefficient of the component, or rendering the surface compatible with any of various proteins or other substances that the surface will contact when in use or that are to adhere or affix to the surface.

The gas used may range from gases that are otherwise inert and do not themselves bond to the polymer to those that are coupling, oxidizing, or reducing reagents and chemically transform the polymer by the addition of groups or atoms. Examples of gases that are useful in activating the surface polymer chains are the noble gases, hydrogen gas, oxygen gas, organic fluorides and hydrocarbons. Preferred among these are argon, helium, hydrogen gas, oxygen gas, and tetrafluoromethane. Examples of gases that are useful in converting the surface polymer chains to increase their hydrophilic character are oxygen gas, acetic acid, volatile siloxanes, ethylene oxide, and hydrocarbons with hydrophilic groups. Examples of gases that are useful in increasing the hydrophobic character of the surface polymer chains are organic fluorides, particularly trifluoromethane ($HCF_3$), tetrafluoromethane ($CF_4$), tetrafluoroethane ($C_2H_2F_4$), hexafluoroethane ($C_2F_6$), difluoroethylene ($C_2H_2F_2$), and hexafluoropropylene ($C_3F_6$), as preferred organic fluorides, and tetrafluoroethane, hexafluoroethane, and hexafluoropropylene as the most preferred. These species can be used individually or as mixtures. Preferred atomic ratios of carbon:fluorine in the treatment gas are in the range of 2:1 to 3:1.

When organic fluorides are used as the treatment gas, it may also be desirable to include in the treatment gas a fluorine scavenger to control the degree of etching on the polymer surface. Examples of fluorine scavengers are hydrogen gas, sulfuric acid gas, methane or mixtures of these gases. Preferred mixtures of gases for use as the treatment gas are $CF_4/H_2$, $CF_4/CH_4$, $C_2H_2F_2/CH_4$, $CHF_3/CH_4$, $C_2H_2F_4/CH_4$, $C_2F_6/CH_4$, and $C_2F_6/CH_4$.

The power applied to convert the gas to plasma form will likewise be selected in accordance with the effect sought to be achieved and the desired depth to which the effect will penetrate below the surface into the bulk of the polymer. Penetration depths may be less than one millimeter, or within the range of 1–10 mm or greater. In most applications, best results will be obtained using a power density, expressed in terms of wattage per unit area of the surface to be treated, ranging from about 2 to about 100 watts per square centimeter, preferably from about 5 to about 50 watts per square centimeter, and more preferably from about 3 to about 30 watts per square centimeter. When conversions are preceded by activation of the polymer, typical power densities for the preliminary activation step may range from about 1 to about 10 watts per square centimeter, preferably from about 2 to about 5 watts per square centimeter.

Other treatment conditions are likewise variable and are not critical to the novelty or utility of the invention. The exposure time for example will be selected with the considerations similar to those used for the power density. In most applications, best results will be obtained with exposure times ranging from about 2 minutes to about 60 minutes, and preferably from about 4 minutes to about 30 minutes. When activation of the polymer is performed as a preliminary step, typical exposure times for the preliminary activation step may range from about 0.5 minute to about 20 minutes, preferably from about 1 minute to about 5 minutes. The pressure in the plasma chamber will likewise be subject to similar considerations, with best results generally obtainable at a pressure within the range of about 50 mtorr (6.65 pascals) to about 250 mtorr (33.2 pascals), preferably from about 80 mtorr (10.6 pascals) to about 230 mtorr (30.6 pascals), and more preferably from about 80 mtorr (10.6 pascals) to about 130 mtorr (17.3 pascals). The flow rate of the plasma gas across the workpiece surface being treated may likewise vary, typically from about 50 to about 2000 cubic centimeters per second (measured under standard conditions of temperature and pressure, and expressed as sccm), and preferably from about 100 sccm to about 1000 sccm. Optimal flow rates within these ranges will vary with the size of the treatment chamber. The treatment does not require elevated temperature and is readily performed at temperatures less than 50° C., preferably from about 20° C. to about 40° C.

Plasma treatments in accordance with this invention can be combined with plasma treatments for other purposes, such as sterilization of the polymer surface, removal of contaminants by etching away weakly bonded molecules, alteration of the surface topography, or increasing surface biocompatibility. Sterilization, for example, can be achieved by a five-minute treatment with hydrogen peroxide plasma, which is preferable to conventional sterilization methods such as gamma radiation that require post-processing and cause long-term degradation of the bulk properties of the polymer. Surface roughness can be altered by etching away surface material, and biocompatibility can be increased by treatment with ammonia.

This invention is applicable to high molecular weight polymers in general that are disclosed for use in the literature, or otherwise known to be useful, in manufacturing components of orthopedic implants or components of other medical or clinical devices. For artificial knee and hip joints, the polymer that is currently of the greatest interest is ultra high molecular weight polyethylene (UHMWPE), particularly those grades with molecular weights ranging from about 35,000 to about 6,000,000 g/mole, a crystallinity of 0–90%, and a density of about 0.91 to about 0.98 g/mL. Further descriptions of this material and similar materials are found in Li, S., et al., "Current Concepts Review—Ultra High Molecular Weight Polyethylene: The Material and Its Use in Total Joint Implants," *The Journal of Bone and Surgery*, vol. 76-A, no. 7, pp. 1080–1090 (July 1994), and Kurtz, S. M., et al., "Advances in the processing, sterilization, and crosslinking of ultra-high molecular weight polyethylene for total joint arthroplasty," *Biomaterials*, vol. 20, pp. 1659–1688 (1999). The contents of these papers are incorporated herein by reference. Other polymers of interest that this invention is applicable to are high-density polyethylene, medium-density polyethylene, low-density polyethylene, polymethylmethacrylate, silicones, and polyurethanes.

As noted above, the plasma is generated by any form of high-energy radiation that will plasma the treatment gas in plasma form. Radio-frequency and ultraviolet radiation are examples; radio-frequency energy is preferred.

Although this invention is of broad application, it is of particular interest in the manufacture of component parts for articulatable prosthetic implants that include a polymeric component with a surface that is in sliding contact with a second component that is often constructed of a metallic or ceramic material. An example of such an implant is a knee implant in which the polymeric component whose surface is to be treated in accordance with this invention is an acetabular cup over an annular area of a metallic femoral head. The femoral head, which is generally referred to as a "counter-bearing surface," may be constructed of metal, ceramic, or polymeric material which may be the same or a different polymer than that of the acetabular head. Common materials for the femoral head are ceramics and metal alloys such as CoCr and $Ti_6Al_4V$. This invention is useful in enhancing the tribological characteristics of the polymer acetabular head.

The following examples are offered only as illustration and are not intended to limit the scope of the invention.

EXAMPLE 1

This example illustrates the use of plasma treatments in accordance with this invention in three multi-step treatment protocols on disks of UHMWPE, using a fluorocarbon plasma in two of the protocols and oxygen gas in the third.

Flat, circular disks measuring 3.0 inches in diameter (7.6 cm diameter, 45.6 $cm^2$ area) were machined from medical-grade UHMWPE (GUR 415, Hoechst Celanese), and were polished, then degreased, and finally cleaned by ultrasound. The disks were the exposed to various plasma treatments in accordance with the invention, using 13.56-MHz radio frequency (RF) plasma discharges. The conditions for each treatment are listed in Table I, in which the exposure time for each plasma treatment is expressed in minutes, the power density is expressed as watts per unit area (square centimeter) of disk surface, and the flow rate of the treatment gas is expressed in standard cubic centimeters per minute (sccm).

TABLE I

Plasma Treatment Conditions

| Treatment | Step | Gas | Time (minutes) | Power Density (W/cm$^2$) | Gas Flow Rate (sccm) | Pressure (mtorr) |
|---|---|---|---|---|---|---|
| 1-A | 1 | Ar | 1 | 4.4 | 490 | 228 |
|  | 2 | $C_3F_6$ | 5 | 8.8 | 100 | 88 |
|  | 3 | $C_3F_6$ | 1 | 0 | 200 | 129 |
|  | 4 | Ar | 2 | 0 | 490 | 217 |
| 1-B | 1 | Ar | 1 | 4.4 | 490 | 227 |
|  | 2 | $C_3F_6$ | 5 | 7.7 | 100 | 85 |
|  | 3 | $C_3F_6$ | 1 | 0 | 200 | 129 |
|  | 4 | Ar | 2 | 0 | 490 | 217 |
| 1-C | 1 | $O_2$ | 1 | 6.1 | 500 | 244 |
|  | 2 | $CH_4$ | 15 | 8.2 | 220 | 156 |

Friction and wear testing were performed by use of a unidirectional sliding pin-on-disk apparatus using rounded and polished CoCrWNi alloy pins having a radius of 3.28 mm. The apparatus consisted of a turntable to support the test disk. The turntable is rotated at 0.1 Hz and the pin is placed over the turntable in contact with the test disk under a controlled load. Four strain gauges in a Wheatstone bridge configuration, together with a suitable amplifier and recorder, are used to measure the strain on the pin resulting from contact with the revolving disk. The coefficient of friction at the disk surface is calculated from the strain measurements. Prior to testing, the disks were coated with a lubricant to approximate the physiological environment of a prosthetic implant in actual use. The lubricant consisted of bovine serum containing 0.1% benzamidine, 0.1% typsin inhibitor, and 0.2% sodium azide (antibacterial agent), all percents by weight. In each experiment, the total sliding distance was 500 m, the applied mean contact pressure was 25 MPa, and the sliding speed was 25 mm/s. The experiments were performed in a clean laboratory environment at an ambient temperature of about 25° C. Wear rates were calculated by dividing the total volume of worn UHMWPE, as determined from cross sectional surface profilometry measurements of the wear track, by the total sliding distance.

The wear rates, expressed as $10^{-13}$ $m^3/m$, and the steady-state coefficients of friction for disks having undergone treatment 1-A and 1-B of Table I, are shown in the bar graph of FIG. 1, in which the wear rates are shown as shaded bars and the coefficients of friction are shown as unshaded bars. The corresponding wear rate and coefficient of friction for a control (untreated) disk are also shown for purposes of comparison. Each bar on the graph represents the mean of four measurements, while the error lines indicate the standard deviation. The coefficient of friction values are shown as the same (0.12) for disks representing treatments 1-A and 1-B as well as the control disk, indicating that the sliding friction behavior was at most only marginally affected by the exposure of the disks to the plasma environment. Some treatments, however, for which the results are not shown in FIG. 1, resulted in a greater coefficient of friction than that of the untreated (UT) disk, while some treatments resulted in unsteady, stick-slip sliding conditions on the disk. These aberrations were most likely due to the presence of a discontinuous surface layer and were circumvented by modifying the process parameters in the final treatment step to those conditions shown in Table I.

The data in FIG. 1 show that wear resistance was greater in disks subjected to treatment 1-A than in the control disk, while wear resistance was lower in disks subjected to treatment 1-B. This is possibly attributable to a less uniform hydrophobic layer or one with less cohesion to the substrate as a result of the relatively low power density of treatment 1-B.

Figure 2:
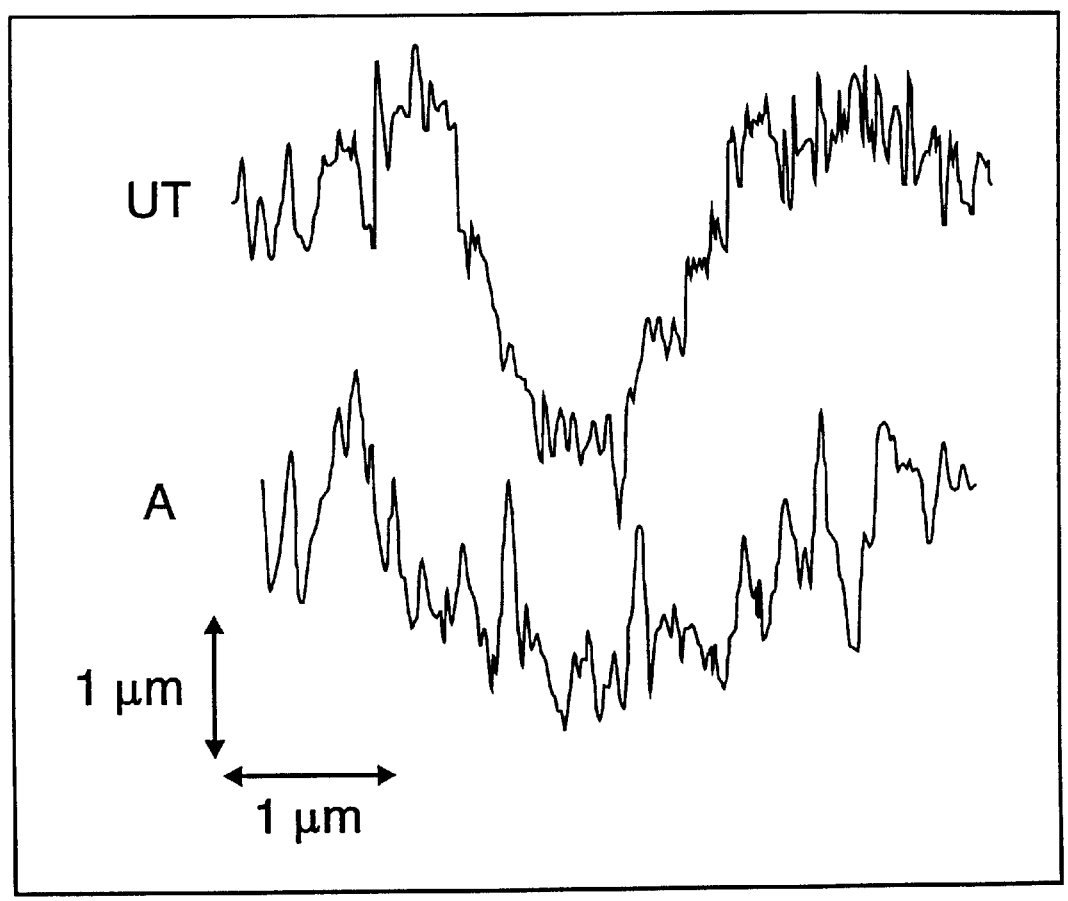
FIG. 2 are surface profilometry scans comparing test samples of UHMWPE treated in accordance with this invention with untreated samples.

Surface profilometry scans are shown in FIG. 2 for one sample of treatment 1-A and for an untreated (UT) disk. The treatment A scan shows a profound improvement in the wear rate.

Further analyses included measurements of the contact angle of advancing distilled water droplets on the disk surfaces, as a measure of the relative degree of hydrophobicity or hydrophilicity. The advancing contact angles for disks representing treatments 1-B and 1-C and for the untreated control disk are listed in Table II.

TABLE II

Contact Angles of Untreated and Plasma-Treated UHMWPE

| Treatment | Contact Angle (degrees) |
|---|---|
| None | 112 |
| 1-B (Table I: Ar/$C_3F_6$) | 148 |
| 1-C (Table I: $O_2$/$CH_4$) | 102 |

Untreated UHMWPE is a hydrophobic polymer. Table II indicates that the disk subjected to treatment C, which consisted of the $O_2$ and $CH_4$ plasma treatments, displayed a considerably reduced contact angle, indicating that the treatment lowered the hydrophobicity of the disk surface. The disk subjected to treatment B, which consisted of the Ar and $C_3F_6$ plasma treatments, displayed an increased contact angle, indicating that the treatment increased the hydrophobicity of the disk surface, which is consistent with the presence of $CF_x$ groups on the surface.

Figure 3:
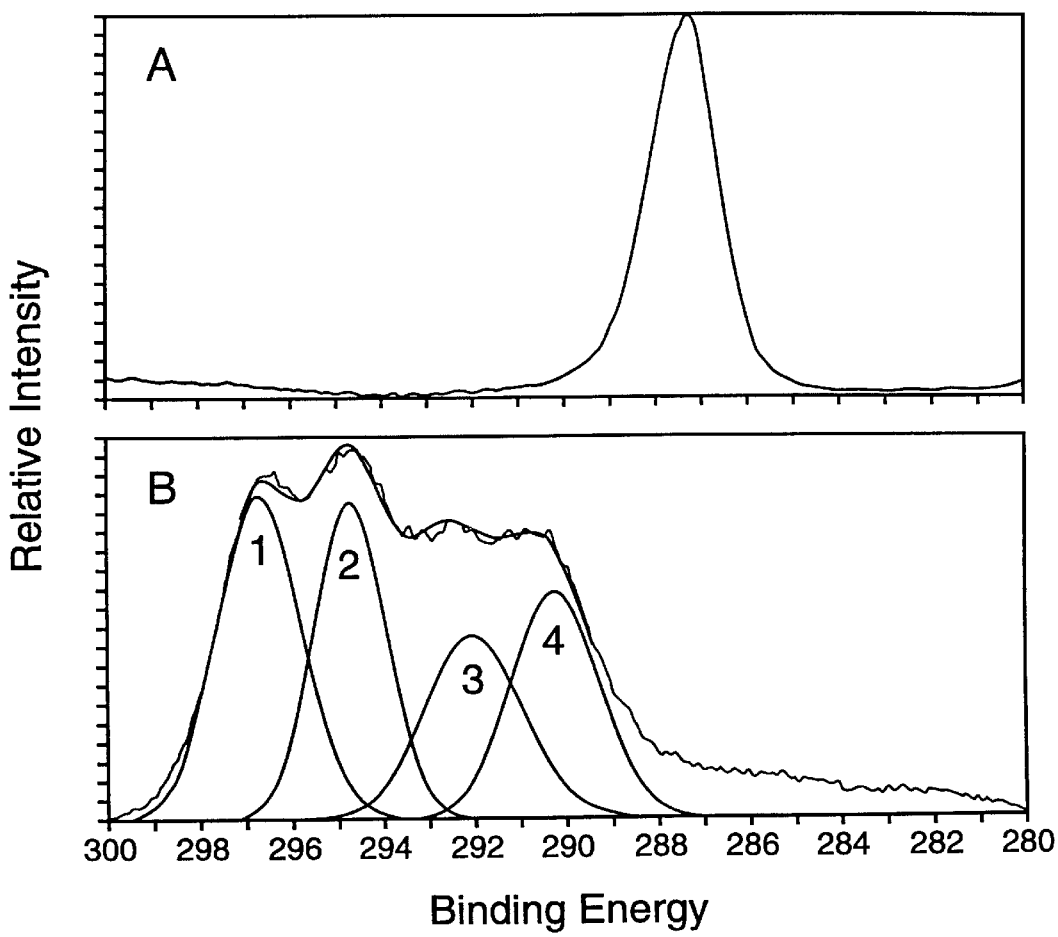
FIGS. 3a and 3b are x-ray photoelectron spectroscopy multiplex scans of an untreated UHMWPE sample (FIG. 3a) and a UHMWPE sample treated in accordance with this invention (FIG. 3b).

Still further data were obtained by performing x-ray photoelectron spectroscopy scans to obtain indications of the chemical composition of the disk surfaces and to identify functional groups bonded to the surfaces during the treatment. FIGS. 3a and 3b show the scans for the untreated disk and a disk subjected to treatment 1-B, respectively. Comparison of these two scans shows that the C 1s peak shifted considerably as a result of the plasma treatment from its otherwise normal value of 285 eV. The shift is attributed to the charging of the polymer under the x-ray source. In the scan of the untreated disk, only the C 1s (~287 eV) peak, the O 1s (~535 eV) peak, and some small impurity peaks were visible. In the scan of the treated disk, the F 1s peak and complementary F peaks are visible, and the C 1s peak is broadened; indicating the formation of multiple $CF_x$ bonds. This is consistent with the expectation that carbon atoms become more positively charged and therefore have a greater binding energy when bonded to the more electronegative fluorine atoms. The peaks labeled 1, 2, 3, and 4 represent —$CF_3$, —$CF_2$, =CF—, and —$CF_2$—$CF_2$—, respectively.

EXAMPLE 2

This example illustrates the use of plasma treatments in accordance with this invention in both single-step and multi-step treatment protocols on disks of UHMWPE, using a fluorocarbon plasma preceded by an argon plasma in one of the protocols, the fluorocarbon plasma alone in a second protocol and the argon plasma alone in the third and fourth protocols. This example also illustrates how the coefficient of friction can be reduced by imposing a plasma treatment for an extended duration and at a higher power density.

The materials and equipment of Example 1 were used, and the conditions of the treatment protocols are listed in Table III.

TABLE III

Plasma Treatment Conditions

| Treatment | Step | Gas | Time (minutes) | Power Density (W/cm$^2$) | Gas Flow Rate (sccm) | Pressure (mtorr) |
|---|---|---|---|---|---|---|
| 2-A | 1 | Ar | 1 | 4.4 | 500 | 221 |
|  | 2 | $C_3F_6$ | 5 | 8.8 | 200 | 104 |
| 2-B |  | $C_3F_6$ | 30 | 11.0 | 40 | 67 |
| 2-C |  | Ar | 10 | 22.0 | 1,500 | 150 |
| 2-D |  | Ar | 10 | 22.0 | 1,500 | 150 |

Figure 4:
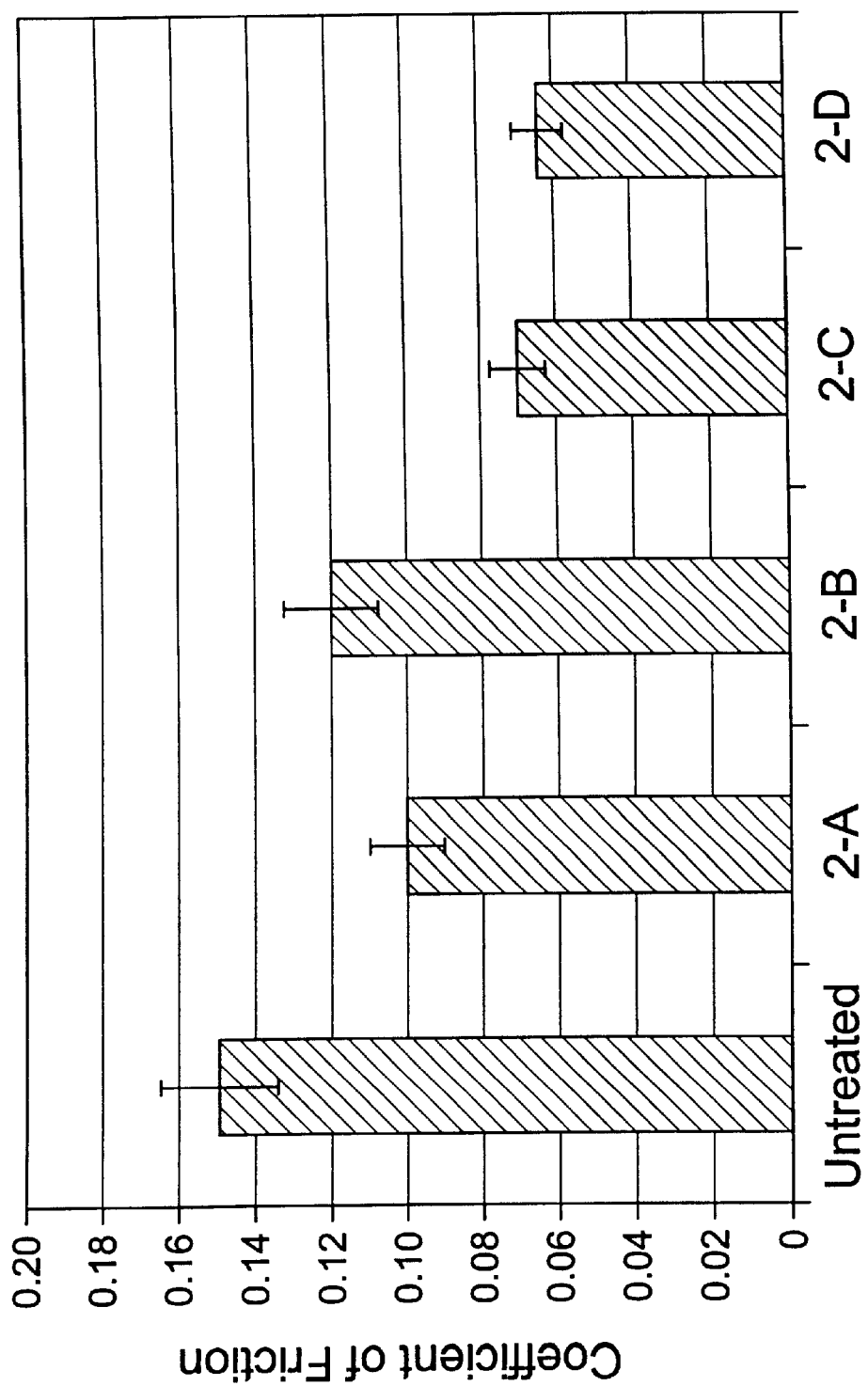
FIG. 4 is a bar graph comparing friction coefficients of test samples of UHMWPE treated in accordance with this invention with friction coefficients of untreated samples.

Friction tests were performed in the same manner as those of Example 1, and the results are shown in FIG. 4. These results indicate that a plasma treatment with an inert gas (argon) at a high power density (22 W/cm$^2$) is more effective in terms of reducing friction than a plasma treatment with a fluorocarbon at low (8.8 W/cm$^2$) and moderate (11.0 W/cm$^2$) power densities, even if the fluorocarbon exposure time is greater than that of the inert gas.

EXAMPLE 3

This example presents further plasma treatments on UHMWPE in accordance with the invention and reports the coefficients of friction (COF) of the surfaces of each of the treated samples. The conditions and results for each treatment are listed in Table IV below, and the results may be compared to untreated UHMWPE for which the coefficient of friction is in the range of 0.12–0.2.

TABLE IV

Plasma Treatment Conditions and Friction Coefficient (COF)

| Treatment | Step | Gas | Time (min) | Power Density (W/cm$^2$) | Gas Flow Rate (sccm) | Pressure (mtorr) | COF After Last Treatment |
|---|---|---|---|---|---|---|---|
| 3-A | 1 | Ar | 1–180 | 4.4–65.8 | 250–1,500 | 65–200 | 0.06–0.13 |
| 3-B | 1 | He | 10–30 | 21.9 | 200–500 | 200 | 0.10 |
| 3-C | 1 | $O_2$ | 1–10 | 6.6 | 500 | 220–250 |  |
|  | 2 | $CH_4$ | 10–30 | 6.6–11.0 | 100–220 | 100–250 | — |
| 3-D | 1 | Ar | 5 | 11.0 | 500 | 220–230 |  |
|  | 2 | $CH_4$ | 10–30 | 6.6–11.0 | 100–500 | 100–250 | — |
| 3-E | 1 | He with 4% $H_2$ (by volume) | 1 | 6.6 | 200 | 140 |  |
|  | 2 | mixture of equal volumes of (i) $CF_4$ and (ii) He with 4% $H_2$ | 20–30 | 6.6–8.8 | 100 | 90–115 | 0.12–0.17 |
| 3-F | 1 | $O_2$ | 1–10 | 6.6–11.0 | 180–200 | 100–250 | 0.14 |
| 3-G | 1 | ethylene oxide | 1–10 | 4.4–11.0 | — | 100–250 | 0.11–0.18 |
| 3-H | 1 | acrylic acid | 1–10 | 4.4–11.0 | — | 100–250 | 0.19 |
| 3-I | 1 | hexamethyldisiloxane | 1–15 | 4.4–8.8 | 140 | 100–400 | 0.18 |
| 3-J | 1 | Ar | 1 | 4.4 | 250–500 | 230 |  |
|  | 2 | $C_3F_6$ | 5–30 | 4.4–11.0 | 50–300 | 60–130 | 0.09–0.16 |
| 3-K | 1 | $C_3F_6$ | 5–30 | 4.4–11.0 | 50–300 | 60–130 | 0.09–0.15 |
| 3-L | 1 | acetylene | 5 | 7.7 | 50 | 30–50 |  |
|  | 2 | $C_3F_6$ | 5 | 8.8 | 500 | 80 | — |
| 3-M | 1 | $O_2/CF_4$ (1:1) | 10 | 9.9 | 500 | 670 |  |
|  | 2 | $C_3F_6$ | 15 | 8.8–9.9 | 50 | 80 | 0.12–0.13 |
| 3-N | 1 | Ar | 5 | 11.0 | 500 | 220–230 |  |
|  | 2 | $CF_4$ | 5–30 | 4.4–11.0 | 100 | 90–120 | 0.12 |

Entries in the COF column that are set forth as ranges represent the range of results for a large number of tests.

Comparing the results in this column with the COF value for the untreated sample in FIG. 4 (0.15), it is seen that certain samples of all of the treatment resulted in a lowering of the COF, and in some cases, notably treatments 3-A and 3-J, the improvement was particularly great.

EXAMPLE 4

This example illustrates the treatment of UHMWPE surfaces to render the surfaces biocompatible.

Coupons of HOSTALEN® GUR 415 UHMWPE (Hoechst Celanese) measuring 9 mm×9 mm×2.5 mm were mechanically polished on one side to a surface finish of $R_a$=0.1 micron. The polished coupons were then ultrasonically cleaned, degreased, and cleaned with argon plasma at ambient temperature, then exposed to various plasma treatments as indicated in Table V.

TABLE V

| | | Plasma Treatment Conditions | | | |
|---|---|---|---|---|---|
| Treatment | Step | Gas | Time (minutes) | Power Density (W/cm$^2$) | Gas Flow Rate (sccm) | Pressure (mtorr) |
| 4-A | 1 | Ar | 15 | 620 | 100 | 203 |
| 4-B | 1 | Ar | 5 | 620 | 100 | 202 |
|  | 2 | $C_3F_6$ | 25 | 560 | 100 | 104 |
| 4-C | 1 | Ar | 5 | 620 | 100 | 200 |
|  | 2 | $CH_4$ | 25 | 495 | 100 | 102 |
| 4-D | 1 | Ar | 5 | 495 | 100 | 180 |
|  | 2 | $NH_3$ | 40 | 495 | 150 | 190 |

Following the treatment, the coupons were sealed in gas-permeable bags and sterilized with a hydrogen peroxide plasma at 400W for 45 minutes. The coupons were then sealed in air-tight bags until they were tested for biocompatibility.

Figure 5:
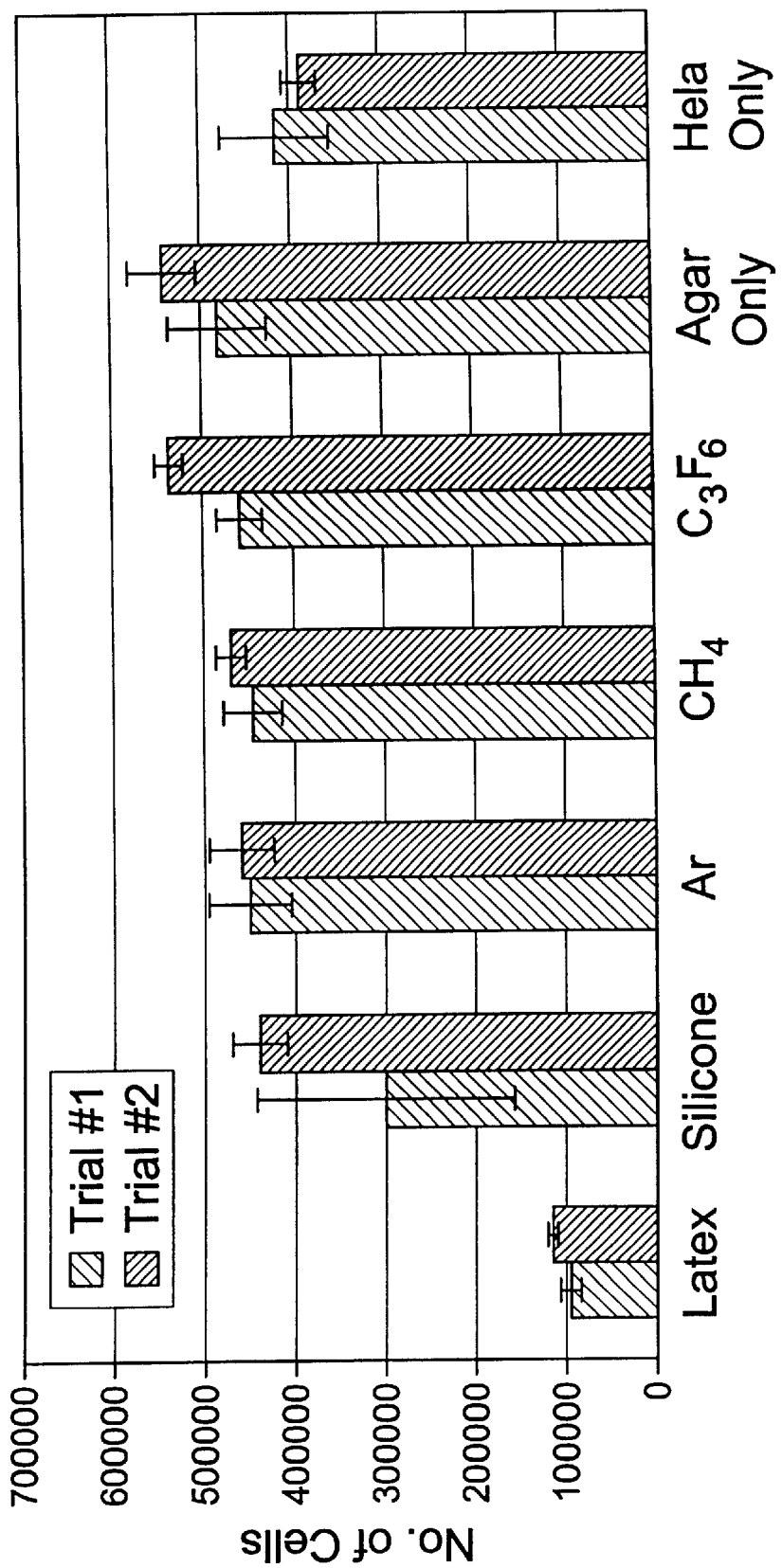
FIG. 5 is a bar graph showing the results of biocompatibility tests on test samples of UHMWPE treated in accordance with the invention and untreated samples.

Quantitative testing for biocompatibility was performed by the 3-(4,5-dimethylthiazol-2-yl)-2,5-diphenyl tetrazolium bromide (MTT) assay of Mossman, T., *J. Immunol. Methods,* vol. 65, pp. 55–63 (1983). According to the assay procedure, the coupons were embedded in 1% agar in 24-well tissue culture plates leaving only the polished surface exposed. One milliliter of Hela cell solution at a concentration of 3.4×10$^5$ cells/mL was then added to each well and the well contents were incubated at 37° C. A positive control test was performed by substituting latex for the agar, and a negative control test was performed by substituting silicone. Additional negative control data was gathered from wells containing only the agar and from wells containing only Hela cells. The number of cells remaining after 24 hours was then determined by reading the absorbance in all wells by spectrophotometer at a wavelength of 570 nm. The results, including two trials, each result representing an average of three coupons, are shown in FIG. 5, which is a bar graph indicating the viability of the Hela cells after being subjected to the various treatments. The graph indicates that none of the plasma treatments adversely affected the Hela cell population. Each of the plasma-treated coupons performed as well as the untreated coupons and as well as the negative silicone control.

Figure 6:
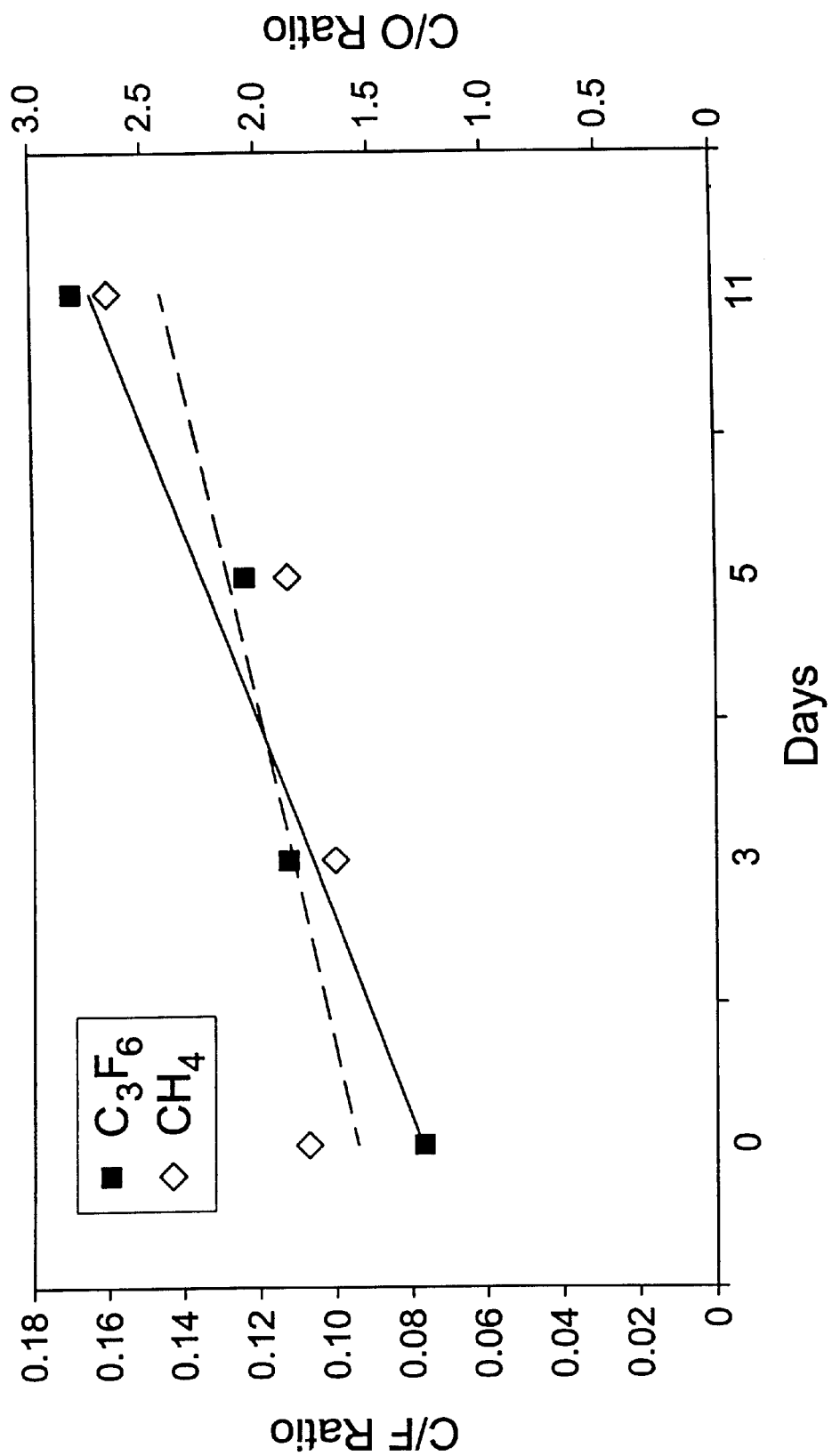
FIG. 6 is a plot of x-ray photoelectron spectroscopy data taken from surface scans of test samples of UHMWPE treated in accordance with the invention.

Evolution of the surface chemistry was monitored using an x-ray photoelectron spectrophotometer (XPS) (SSM 660, Physical Electronics Incorporated, Eden Prairie, Minn., USA). The $C_3F_6$-treated samples were scanned at 0, 1, 4, 7 and 10 days in air. The $CH_4$-treated samples were scanned at 0, 2, 3, 9 and 12 days in air. The XPS results are shown in FIG. 6, which is a plot of the C/F ratio and the C/O ratio as functions of the number of days of exposure to air. In the Figure, the solid line represents the $C_3F_6$-treated coupons and the dashed line represents the $CH_4$-treated coupons. The data points demonstrate that $C_3F_6$ and $CH_4$ treatments evolve with exposure to air. For the $C_3F_6$ treated samples, the C/F ratio increases over time, indicating a net loss of fluorine on the surface. More detailed scans (not shown in FIG. 6) indicate the loss of $CF_3$ groups at early times. The $CH_4$ samples show an increase in the C/O ratio, indicating a loss of oxygen at the surface. Oxygen is a contaminant of the plasma treatment process. Detailed scans of these samples (not shown in FIG. 6) illustrate the loss of C—O and C=O bonds at the surface as a function of time.

The net loss of fluorine on the $C_3F_6$-treated samples can be attributed to rotation of the hydrophobic $CF_x$ bonds into the UHMWPE bulk. This appears to happen preferentially to the $CF_x$ groups. The loss of oxygen on the surfaces of the $CH_4$-treated samples can be attributed to oxygen diffusion in the bulk, a known behavior of UHMWPE.

These examples and the discussion that precedes them are offered primarily for purposes of illustration. It will be readily apparent to those skilled in the art that further variations of the operating procedures and conditions and substitutions of the materials can be made without departing from the spirit and scope of the invention.

What is claimed is:

1. An articulatable prosthetic implant comprising a polymeric component having a surface in sliding contact with a further component of said implant and a bulk substrate beneath said surface, said polymeric component comprised of a biologically compatible organic polymer with a crosslinking profile normal to said surface, said crosslinking profile defined by a crosslinking density at said surface that is sufficiently great to inhibit crystalline lamella formation at said surface and a crosslinking density in said bulk substrate that is substantially lower than that of said surface, said crosslinking profile produced by a process comprising contacting said surface with a substance in gaseous plasma state at a sufficient power density and for a sufficient exposure time to effect crosslinking of polymer in said polymeric component at said surface.

2. An articulatable prosthetic implant in accordance with claim 1 in which said substance is a member selected from the group consisting of noble gases, hydrogen gas, oxygen gas, organic fluoride gases, and hydrocarbon gases.

3. An articulatable prosthetic implant in accordance with claim 1 in which said substance is a member selected from the group consisting of argon, helium, hydrogen, oxygen, and tetrafluoromethane.

4. An articulatable prosthetic implant in accordance with claim 1 in which said biologically compatible organic polymer is ultra high molecular weight polyethylene with a molecular weight ranging from about 35,000 to about 6,000,000.

5. An articulatable prosthetic implant in accordance with claim 1 in which said power density ranges from about 1 to about 10 watts per square centimeter of said surface, said exposure time ranges from about 0.5 minute to about 20 minutes, and said contacting of said surface with said substance in gaseous plasma state is performed at a pressure ranging from about 50 mtorr to about 250 mtorr.

6. An articulatable prosthetic implant in accordance with claim 1 in which said power density ranges from about 2 to about 5 watts per square centimeter of said surface, said exposure time ranges from about 1 minute to about 5 minutes, and said contacting of said surface with said substance in gaseous plasma state is performed at a pressure ranging from about 80 mtorr to about 130 mtorr.

7. An articulatable prosthetic implant comprising a polymeric component having a surface in sliding contact with a further component of said implant, said polymeric component comprised of a biologically compatible organic polymer with organic fluoride groups bonded thereto at said surface at sufficient density to improve resistance of said polymeric component to wear, said organic fluoride groups bonded to said polymer by a process comprising contacting said surface with an organic fluoride in gaseous plasma state at a sufficient power density and for a sufficient exposure time to effect bonding of said organic fluoride to said surface.

8. An articulatable prosthetic implant in accordance with claim 7 in which said organic fluoride is a member selected from the group consisting of trifluoromethane, tetrafluoromethane, tetrafluoroethane, hexafluoroethane, difluoroethylene, and hexafluoropropylene.

9. An articulatable prosthetic implant in accordance with claim 7 in which said organic fluoride is a member selected from the group consisting of tetrafluoroethane and hexafluoroethane.

10. An articulatable prosthetic implant in accordance with claim 7 in which said organic fluoride is hexafluoropropylene.

11. An articulatable prosthetic implant in accordance with claim 7 in which said biologically compatible organic polymer is ultra high molecular weight polyethylene with a molecular weight ranging from about 35,000 to about 6,000,000.

12. An articulatable prosthetic implant in accordance with claim 7 in which said power density ranges from about 2 to about 100 watts per square centimeter of said surface, said exposure time ranges from about 2 minutes to about 60 minutes, and said contacting of said surface with said organic fluoride in gaseous plasma state is performed at a pressure ranging from about 50 mtorr to about 250 mtorr and at a temperature of less than 50° C.

13. An articulatable prosthetic implant in accordance with claim 7 in which said power density ranges from about 5 to about 50 watts per square centimeter of said surface, said exposure time ranges from about 4 minutes to about 30 minutes, and said contacting of said surface with said organic fluoride in gaseous plasma state is performed at a pressure ranging from about 80 mtorr to about 230 mtorr and at a temperature of less than 50° C.

14. An articulatable prosthetic implant in accordance with claim 7 in which said power density ranges from about 8 to about 30 watts per square centimeter of said surface, said exposure time ranges from about 4 minutes to about 30 minutes, and said contacting of said surface with said organic fluoride in gaseous plasma state is performed at a pressure ranging from about 80 mtorr to about 130 mtorr and at a temperature within the range of about 10° C. to about 50° C.

\* \* \* \* \*